(12) United States Patent
Inokuchi

(10) Patent No.: US 6,753,399 B2
(45) Date of Patent: Jun. 22, 2004

(54) METHOD FOR THE PREPARATION OF FINE GLOBULAR SILICONE RESIN PARTICLES

(75) Inventor: Yoshinori Inokuchi, Matsuida-machi (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/918,465

(22) Filed: Aug. 1, 2001

(65) Prior Publication Data

US 2002/0016434 A1 Feb. 7, 2002

(30) Foreign Application Priority Data

Aug. 2, 2000 (JP) ........................................ 2000-234105

(51) Int. Cl.⁷ ............................................... C08G 77/08
(52) U.S. Cl. ........................... 528/14; 528/21; 556/482; 556/458
(58) Field of Search ..................... 528/21, 14; 556/482, 556/458

(56) References Cited

U.S. PATENT DOCUMENTS 5,086,145 A 2/1992 Morimoto et al.
5,801,262 A * 9/1998 Adams

FOREIGN PATENT DOCUMENTS

| EP | 09374965 A | | 8/1999 |
|---|---|---|---|
| JP | 06-122516 | * | 6/1994 |
| JP | 11-181095 | * | 7/1999 |
| JP | 934 965 | * | 8/1999 |
| JP | 2000-017074 | * | 1/2000 |

OTHER PUBLICATIONS

Database WPI, Derwent Publication, Ltd., London, GB; AN 1994–186263, XP002247303 & JP 06 122516 A (Tokuyama Soda), May 6, 1994 "abstract" European Search Report.

* cited by examiner

*Primary Examiner*—Kuo-Liang Peng
(74) *Attorney, Agent, or Firm*—Millen White Zelano & Branigan, P.C.

(57) ABSTRACT

The invention discloses a novel method for the preparation of globular particles of a silicone resin or, in particular, a polyorganosilsesquioxane resin having properties suitable as an adjuvant in hair-care toiletry preparations by the hydrolysis condensation reaction of an organotrialkoxy silane compound such as methyl trimethoxysilane in an aqueous alkaline medium. Characteristically, the aqueous reaction medium is alkalified with ammonia or, preferably, an amine compound, e.g., mono(n-alkyl) amine compound, to have a specified pH value of 10.0 to 13.0 and the hydrolysis condensation reaction of the starting silane compound in the aqueous medium is conducted in the presence of metallic ions or, in particular, magnesium ions in a specified concentration of $1 \times 10^{-5}$ to $1 \times 10^{-2}$ mole/liter.

6 Claims, No Drawings

METHOD FOR THE PREPARATION OF FINE GLOBULAR SILICONE RESIN PARTICLES

BACKGROUND OF THE INVENTION

The present invention relates to a novel method for the preparation of fine globular particles of a silicone resin. More particularly, the invention relates to a method for the preparation of globular particles of a polyorganosilsesquioxane resin having a relatively large average particle diameter.

As is well known, powders of fine globular silicone resin particles are widely employed as an adjuvant material, for example, in plastic resin-based molding compositions to Impart slipperiness, abrasion resistance and light diffusibility and to impart anti-blocking surface to resin films, in rubber compositions to impart surface slipperiness and lubricity to rubber articles or coating thereof, in cosmetic or toiletry preparations and waxes to impart spreadability, surface lubricity and water repellency and in detergents as a grindability-imparting additive.

Needless to say, the requirements for the characteristics of the silicone resin particles are different depending on the intended applications of the particles. For example, silicone resin particles used as an additive in plastic resins to impart surface slipperiness and antiblocking nature of the surfaces are required to have a globular or spherical particle configuration with a relatively large average particle diameter.

A great variety of methods are proposed and practiced heretofore for the preparation of fine silicone resin particles having a globular particle configuration including the methods outlined below. Belgian Patent No. 572412 discloses a method in which methyl trichlorosilane is added dropwise into water under agitation to effect hydrolysis condensation reaction of the silane compound. Japanese Patent Kokai No. 6-157759 teaches that an organotrichlorosilane is dissolved in a solution of an alkali hydroxide followed by the addition of an acid to the solution to effect hydrolysis and condensation reaction of the silane compound. These methods, however, are not suitable when silicone resin particles having a globular particle configuration are desired.

A method is proposed in Japanese Patent Kokai No. 6-179751 according to which an organotrichlorosilane is added to an aqueous solution saturated with hydrogen chloride to effect hydrolysis condensation reaction of the silane compound. This method, however, has a disadvantage of low productivity because it is an extremely complicated and time-consuming procedure to completely remove hydrogen chloride from the product of resin particles.

Further, Japanese Patent Publication No. 52-12219 discloses a method in which an organotrialkoxy silane is added to an acidic or alkaline aqueous solution containing an ionic surfactant to effect hydrolysis condensation reaction of the silane compound. Japanese Patent Publication No. 1-14250 proposes a method according to which an organotrialkoxy silane or a partial hydrolysis-condensation product thereof is dispersed and emulsified in an aqueous medium containing non-ionic and cationic surfactants and then subjected to the hydrolysis condensation reaction with addition of an alkaline compound. Japanese Patent Kokai No. 4-359022 proposes a method in which an alkali metal salt of an organosilanol compound is neutralized with an acid in an aqueous solution and subjected to condensation reaction. These methods, however, are not suitable when the silicone resin particles obtained thereby are desired to have a relatively large average particle diameter.

Besides, a proposal is made in Japanese Patent Kokai No. 63-308067, according to which an organotrialkoxy silane or a partial hydrolysis condensation product thereof is gradually added dropwise into an aqueous solution containing a surfactant to effect hydrolysis condensation reaction and the thus obtained aqueous colloidal suspension of the silicone resin particles is spray-dried. The thus obtained particles have a particle diameter of 1 to 100 $\mu$m and are each an agglomerate of primary particles having a particle diameter of 10 to 150 nm. The powder of such agglomerated resin particles has a problem that the agglomerated particles are subject to disintegration when a composition compounded therewith is worked under a high shearing force if not to mention the disadvantage of low productivity of the process including the step of spray drying of an aqueous colloidal suspension of which the solid concentration is usually low.

Japanese Patent Kokai No. 4-33927 proposes a method in which, by using a non-ionic surfactant as the dispersing agent, an organotrialkoxy silane or a partial hydrolysis condensation product thereof is dispersed and suspended in a non-aqueous dispersion medium in the presence of a basic or acidic catalyst to effect hydrolysis condensation reaction. Since the dispersion medium is non-aqueous, this method is economically disadvantageous.

A method is disclosed in Japanese Patent Kokai No. 6-279589, according to which an organopolysiloxane is dissolved in an aqueous solution of an alkali metal hydroxide and the solution is subjected to an ion exchange treatment to remove the anions followed by a condensation reaction in the solution having a pH value of 10 or higher at a temperature of 50° C. or higher. The disadvantage involved in this method is the low productivity of the process because the organopolysiloxane as the starting material must be prepared beforehand by conducting the hydrolysis condensation reaction of a hydrolyzable organosilane compound.

Other methods heretofore proposed include: a method in which a methyl trialkoxy silane is added under agitation to an aqueous solution of an alkali metal hydroxide, ammonia or an amine compound to effect hydrolysis condensation reaction (see Japanese Patent Publication No. 40-16917), a method in which a methyl trialkoxy silane or a partial hydrolysis condensation product thereof is added to an aqueous solution of an alkaline earth metal hydroxide or an alkali metal carbonate to effect the hydrolysis condensation reaction (see Japanese Patent Publication No. 56-39808), a method in which a methyl trialkoxy silane compound or a partial hydrolysis condensation product thereof is subjected to the hydrolysis condensation reaction in an aqueous solution of ammonia or an amine compound followed by heating at 70 to 80° C. to promote the condensation reaction and the reaction product is washed with water and dried followed by disintegration into a powder (see Japanese Patent Publication No. 2-22767), a method in which an organotrialkoxy silane compound is dissolved in an aqueous solution of a carboxylic acid followed by the condensation reaction in an alkaline aqueous solution (see Japanese Patent Kokai No. 3-244636), a method in which an organotrialkoxy silane compound dissolved in an organic solvent is mixed with an acidic aqueous solution to effect hydrolysis followed by the addition of a basic compound to the reaction mixture to effect the condensation reaction (see Japanese Patent Kokai No. 6-65378), a method in which a hydrolyzable organometallic compound is subjected to the hydrolysis condensation reaction in a liquid medium consisting of a hydrolysis catalyst, water, an electrolyte and an organic solvent (see Japanese Patent Kokai No. 6-122516), a method in which an organoalkoxy silane compound is subjected to the hydrolysis condensation reaction in the presence of an aqueous solution containing a non-ionic surfactant and ammonia and/or an amine compound (see Japanese Patent Kokai No. 11-152336) and a method in which an organoalkoxy silane compound is subjected to the hydrolysis condensation reaction in an aqueous solution containing an anionic surfactant and ammonia and/or an amine compound (see Japanese Patent Kokai No. 11-181095).

According to these methods, fine organopolysiloxane particles having a particle diameter suitable for the above mentioned applications can be obtained with a high efficiency. When a still larger particle diameter is desired of the organopolysiloxane particles, for example, from methyl trimethoxysilane as the starting material, particles having an average particle diameter not smaller than 3 $\mu$m can be obtained by decreasing the amount of the alkaline catalytic compound though with a problem that the amount of agglomerates is increased unavoidably.

With an object to solve this problem for obtaining organopolysiloxane particles by using the alkaline catalyst in a decreased concentration without agglomerate formation, improvements are proposed by conducting the condensation reaction under weak agitation or without agitation of the reaction mixture including: a method in which the hydrolysis condensation reaction of a methyl trialkoxysilane compound or a partial hydrolysis condensation product thereof is conducted by keeping the reaction mixture separated into two layers with the reactant forming the upper layer and the aqueous hydrolysis medium containing ammonia or an amine compound forming the lower layer under weak agitation (see Japanese Patent Publication No. 4-70335), a method in which a methyl trialkoxy silane compound or a partial hydrolysis condensation product thereof and water are agitated to form a uniform mixture to which an alkaline compound is added subsequently to effect the hydrolysis condensation reaction (see Japanese Patent Kokai No. 4-88023 and No. 6-248081) and a method in which an organotrialkoxy silane compound is hydrolyzed in an acidic condition to give a hydrated alcoholic solution which is then admixed with an aqueous alkaline solution to effect the condensation reaction without agitation (see Japanese Patent Kokai No. 10-45914). Further, fine particles without agglomerates can be obtained by the addition of a dispersion stabilizer to the reaction mixture even with a low concentration of the alkaline catalyst as in the method disclosed in Japanese Patent Kokai No. 11-92560 in which an organotrialkoxysilane compound is added to an aqueous solution containing an anionic surfactant, a polymeric stabilizer and a hydroxyl base to effect the hydrolysis condensation reaction.

A serious disadvantage when the concentration of the alkaline catalyst is low is that particles having a desired particle diameter can hardly be obtained with goof reproducibility. Further, the amount of the starting organoalkoxy silane compound subjected to the reaction cannot be large enough in order to suppress formation of agglomerates resulting in problems of low productivity of the process and a large residual amount of silanol groups. Japanese Patent Kokai No. 2000-17074 proposes a method for obtaining particles of a relatively large particle diameter from an organoalkoxy silane compound by seed polymerization but this method is also not free from the above mentioned problems because of the low concentration of the alkaline catalytic compound.

SUMMARY OF THE INVENTION

The present invention accordingly has an object, in view of the above described problems and disadvantages in the prior art methods, to provide an improved method for the preparation of globular polyorganosilsesquioxane particles having a relatively large particle diameter of 3 to 30 $\mu$m from an organotrialkoxy silane compound as the starting material with little formation of agglomerates in the presence of an alkaline catalytic compound in a relatively high concentration and with good reproducibility of the particle diameter even by increasing the charging amount of the starting silane compound into the reaction medium without decreasing the productivity.

Thus, the method of the present invention for the preparation of globular particles of a silicone resin comprises the steps of:

preparing an aqueous alkaline solution having a pH value in the range from 10.0 to 13.0 by the addition of a basic compound selected from the group consisting of ammonia and water-soluble amine compounds to water;

adding a water-soluble electrolytic compound of a metal to the aqueous alkaline solution in a concentration of the metallic ions in the range from $1\times10^{-5}$ to $1\times10^{-2}$ mole/liter; and adding, to the aqueous alkaline solution, an organotrialkoxy silane compound or a partial hydrolysis condensation product thereof as the starting material under agitation to effect hydrolysis condensation reaction of the starting material.

It is preferable that the electrolytic compound of a metal is a water-soluble magnesium compound and the aqueous solution is alkalified with an amine compound which is a monoalkyl amine compound. When these requirements are satisfied, the globular polyorganosilsesquioxane particles have an average particle diameter in the range from 3 to 30 $\mu$m with good reproducibility.

DETAILED DESCRIPTION OF THE PREFERRED EMBODIMENTS

The silicone resin forming the globular silicone resin particles according to the inventive method is a polyorganosilsesquioxane resin consisting of the trifunctional siloxane units expressed by the unit formula $R^1SiO_{3/2}$, in which $R^1$ is a monovalent hydrocarbon group having 1 to 20 carbon atoms. Examples of the group denoted by $R^1$ include alkyl groups such as methyl, ethyl, propyl, butyl, pentyl, hexyl, heptyl, octyl, nonyl, decyl, tridecyl, tetradecyl, hexadecyl, octadecyl and eicosyl groups, aryl groups such as phenyl and tolyl groups, cycloalkyl groups such as cyclobutyl, cyclopentyl and cyclohexyl groups, alkenyl groups such as vinyl and allyl groups and aralkyl groups such as 2-phenylethyl and benzyl groups as well as substituted hydrocarbon groups obtained by replacing a part or all of the hydrogen atoms in the above named unsubstituted hydrocarbon groups with halogen atoms, (meth)acryloxy groups, mercapto groups or cyano groups such as 3,3,3-trifluoropropyl, 2-(perfluorobutyl)ethyl and 2-(perfluorooctyl)ethyl groups. It is preferable that the groups denoted by $R^1$ are selected from methyl and phenyl groups or, in particular, at least 80% of the groups $R^1$ are methyl and/or phenyl groups.

While the polyorganosilsesquioxane forming the silicone resin particles basically consists of the trifunctional siloxane units as is mentioned above, it is optional that the silicone resin further comprises other types of siloxane units including difunctional units of the formula $R^1{}_2SiO_{2/2}$, monofunctional units of the formula $R^1{}_3SiO_{1/2}$ and tetrafunctional units of the formula $SiO_{4/2}$, in which $R^1$ has the same meaning as defined before, each in a limited molar fraction although it is desirable that at least 80% by moles of the overall siloxane units be the trifunctional units.

The globular silicone resin particles obtained by the inventive method should have an average particle diameter in the range from 3.0 to 30 µm. When the average particle diameter thereof is too small, the desired improvements cannot be fully accomplished in respect of slipperiness of the surface, light-diffusibility, blocking prevention, spreadability and grindability while, when too large, in addition to insufficient improvements in these properties, inherently desirable properties of the base materials of the toiletry preparations to which the powder is compounded are adversely affected.

While the starting material in the inventive method is an organotrialkoxysilane compound, the starting material can be a hydrolysis product thereof or a partial hydrolysis condensation product thereof as well as a combination thereof although an organotrialkoxy silane compound is the most preferable, which is represented by the general formula $R^1Si(OR^2)_3$, in which $R^1$ has the same meaning as defined above and $R^2$ is an alkyl group having 1 to 6 carbon atoms including methyl, ethyl, propyl, butyl, pentyl and hexyl groups, of which methyl group is preferable. When di-, mono- or tetrafunctional siloxane units are to be introduced into the polyorganosilsesquioxane each in a limited molar fraction, the starting alkyl trialkoxysilane compound is admixed with a small amount of a dialkoxy silane compound $R^1_2Si(OR^2)_2$, monoalkoxy silane compound $R^1_3SiOR^2$ or silicon tetraalkoxide compound $Si(OR^2)_4$ or a hydrolysis product or partial hydrolysis condensation product thereof, in which $R^2$ is an alkyl group having up to 6 carbon atoms, of which methyl group is preferred.

The aqueous medium in which the hydrolysis condensation reaction of the silane compound or compounds is conducted according to the inventive method is alkalified by the addition of a basic compound including ammonia and water-soluble amine compounds to serve as the catalyst for promoting the reaction. Examples of suitable amine compounds include monoalkyl amines such as monomethyl, monoethyl, monopropyl, monobutyl, monopentyl, monohexyl, monoheptyl, monooctyl, monononyl, monodecyl, monododecyl, monotridecyl, monotetradecyl and monopentadecyl amines as well as dimethylamine, diethylamine, trimethylamine, triethylamine, triethanolamine and ethylenediamine. The basic compound is preferably an alkyl amine compound or, more preferably, a water-soluble mono(n-alkyl) amine compound of which the alkyl group has 2 to 6 carbon atoms.

The alkaline aqueous medium, in which the reaction is performed according to the inventive method, should have a pH value in the range from 10.0 to 13.0 or, preferably, from 10.5 to 12.5 or, more preferably, from 11.0 to 12.0. When the pH value of the aqueous medium is too low, the rate of the hydrolysis condensation reaction of the starting reactant is unduly decreased while, when the pH value is too high, the reaction rate is so great that the resultant silicone resin particles cannot be imparted with a good globular particle configuration.

In order to obtain globular silicone resin particles of a controlled average particle diameter as desired, it is essential in the inventive method that the aqueous reaction medium alkalified with ammonia or an amine compound further contains cations of a metal which can be introduced into the aqueous medium by the addition of a water-soluble electrolytic compound of the metal. Examples of the metal include lithium, sodium, potassium, rubidium, cesium, magnesium, calcium, strontium, barium, scandium, titanium, zirconium, vanadium, aluminum and others, of which magnesium is specifically preferable. The magnesium compound which is added to the aqueous medium can be in the form of magnesium hydroxide, magnesium bromide hexahydrate, magnesium chloride, magnesium chloride hexahydrate, magnesium citrate nonahydrate, magnesium lactate trihydrate, magnesium myristate, magnesium nitrate hexahydrate, magnesium oxalate dihydrate, magnesium secondary phosphate trihydrate, magnesium phosphate octahydrate, magnesium stearate, magnesium sulfate, magnesium sulfate heptahydrate and the like.

It is essential in the inventive method that the concentration of the above mentioned metallic ions in the aqueous alkaline reaction medium is in the range from $1\times10^{-5}$ to $1\times10^2$ mole/liter or, preferably, from $5\times10^{-5}$ to $5\times10^{-3}$ mole/liter. When the concentration of the metallic ions is too low, the average particle diameter of the silicone resin particles cannot be large enough while, when the concentration is too high, an increase is resulted in the formation of agglomerates not to give uniformly globular silicone resin particles.

It is optional in the inventive method that the aqueous alkaline reaction medium is further admixed with a surfactant which can be selected from non-ionic, anionic, cationic and amphoteric surfactants without particular limitations. Examples of suitable non-ionic surfactants include polyoxyethylene alkyl ethers, polyoxyethylene-polyoxypropylene alkyl ethers, polyoxyethylene alkylphenyl ethers, polyoxyethyleneglycol fatty acid esters, sorbitan fatty acid esters, polyoxyethylene sorbitan fatty acid esters, polyoxyethylene sorbit fatty acid esters, glycerin fatty acid esters, polyoxyethylene glycerin fatty acid esters, polyglycerin fatty acid esters, propyleneglycol fatty acid esters, polyoxyethylene castor oils, polyoxyethylene hardened castor oils, polyoxyethylene hardened castor oil fatty acid esters, polyoxyethylene alkylamines, polyoxyethylene fatty acid amide, polyoxyethylene-modified organopolysiloxanes and polyoxyethylene/polyoxypropylene-modified organopolysiloxanes.

Examples of suitable anionic surfactants include alkylsulfuric acid salts, polyoxyethylene alkyl ether sulfuric acid salts, polyoxyethylene alkylphenyl ether sulfuric acid salts, N-acyl tauric acid salts, alkylbenzene sulfonic acid salts, polyoxyethylene alkylphenyl ether sulfonic acid salts, α-olefin sulfonic acid salts, alkylnaphthalene sulfonic acid salts, alkyl diphenyl ether disulfonic acid salts, dialkyl sulfosuccinic acid salts, monoalkyl sulfosuccinic acid salts, polyoxyethylene alkyl ether sulfosuccinic acid salts, fatty acid salts, polyoxyethylene alkyl ether acetates, N-acyl amino acid salts, alkenyl succinates, alkylphosphoric acid salts and polyoxyethylene alkyl ether phosphoric acid salts. Examples of suitable cationic surfactants include alkyl trimethylammonium salts, dialkyl dimethylammonium salts, alkyl benzyl dimethylammonium salts, alkylpyridinium salts, monoalkylamine salts and monoalkylamidoamine salts. Examples of suitable amphoteric surfactants include alkyl dimethylamine oxides, alkyl dimethylcarboxy betaines, alkylamidopropyl dimethylcarboxy betaines, alkylhydroxysulfo betaines and alkylcarboxymethyl hydroxyethyl imidazolinium betaines.

The concentration of the above described surfactants in the aqueous alkaline reaction medium, when added, should not exceed 2.0% by weight or, preferably, should not exceed 1.0% by weight. When the concentration of the surfactant is too high, difficulties are encountered in obtaining particles of a relatively large particle diameter in addition to the problem of increased agglomeration of the primary particles not to give a uniformly globular particle configuration.

The temperature of the aqueous alkaline reaction medium, in which the starting material, i.e. an organotrialkoxy silane compound or a hydrolyzate or partial hydrolysis condensation product thereof is subjected to the hydrolysis condensation reaction, is in the range from 0 to 40° C. or, preferably, from 0 to 25° C. An aqueous medium at a temperature lower than 0° C. is naturally in a frozen state not to allow agitation of the reaction medium. When the temperature of the aqueous medium is too high, an increase is caused in the agglomeration of the primary particles not to give a uniformly globular configuration of the particles.

While the starting material is added to the aqueous alkaline reaction medium and dispersed therein by agitation to effect the hydrolysis condensation reaction, the intensity of agitation should not be too vigorous because agglomeration of primary particles is increased under too vigorous agitation not to give a uniformly globular particle configuration. In this regard, the stirrer to disperse the starting material in the aqueous medium is a screw-blade stirrer or a flat-blade stirrer which exhibits a relatively low efficiency of agitation.

In conducting the hydrolysis condensation reaction of the starting material according to the inventive method, the amount of the starting material introduced into the aqueous reaction medium is in the range from 5 to 100 parts by weight or, preferably, from 10 to 50 parts by weight per 100 parts by weight of the aqueous reaction medium. When the amount of the starting material is too small, the productivity of the process cannot be high as a matter of course while, when the amount of the starting material is too large, a uniformly globular configuration of the product particles can hardly be obtained due to an increase in the agglomeration of the primary particles.

While the starting material is introduced into the aqueous alkaline reaction medium to be dispersed therein and subjected to the hydrolysis condensation reaction according to the inventive method, it is preferable that the starting material is introduced into the reaction medium at a relatively low rate, for example, dropwise. Though dependent on various factors such as types of the starting material, pH and temperature of the aqueous medium, intensity of agitation of the medium, overall volume of the starting material and others, the length of time taken for the addition of whole volume of the starting material into the reaction medium is preferably in the range from 30 minutes to 100 hours. When the length of time taken for introduction of the starting material into the reaction medium is too short or too long, a uniformly globular configuration of the particles can hardly be obtained due to increased agglomeration of the primary particles. Nevertheless, it is optional that the whole volume of the starting material is added to the reaction medium at one time if the organotrialkoxysilane as the starting material has a specific gravity lower than that of the aqueous reaction medium and the intensity of agitation of the reaction mixture is kept so low during introduction of the silane compound that the reaction mixture is separated into two layers with the silane compound forming the upper layer floating on the aqueous medium as the lower layer. It is also optional that, when two kinds or more of different silane compounds are employed in combination, the silane compounds are blended together beforehand or the silane compound is switched from one to the other or the mixing proportion thereof is changed in the course of introduction of the starting material into the aqueous reaction medium.

It is desirable that agitation of the reaction mixture is continued for a length of time after completion of dropwise addition of the starting material into the aqueous reaction medium in order to ensure completeness of the hydrolysis condensation reaction. If necessary, the hydrolysis condensation reaction of the starting material can be promoted by increasing the temperature of the reaction mixture, optionally, followed by the addition of an acidic compound to neutralize the alkaline reaction medium.

By completing the hydrolysis condensation reaction of the starting material in the above described manner, the globular silicone resin particles as the product of the inventive method are obtained in the form of an aqueous dispersion of the particles in an aqueous reaction medium containing an alcohol compound as a by-product formed by the hydrolysis reaction of the alkoxy groups in the starting material. Accordingly, it is necessary for most applications that the silicone resin particles are freed from the aqueous medium by a known method such as heating under normal or reduced pressure, gravity settling of the particles in the aqueous dispersion kept standing, fluidization of wet particles in a hot air stream, spray drying of the dispersion and utilization of a fluidizing heating medium following a conventional solid-liquid separation procedure such as filtration, centrifugation, decantation and the like to remove at least a part of the aqueous medium. When the thus dried resin particles are in the form of loose cakes, it is usual that the cakes are disintegrated into discrete particles by using a conventional disintegrator such as jet mills, ball mills, hammer mills and the like.

If an improvement is desired to increase water repellency and slipperiness of the thus dried resin particles, it is optional that the resin particles are subjected to a surface treatment by using a silylating agent, silicone oil, wax, paraffin, fluorocarbon compound and the like.

In the following, the method of the present invention is described in more detail by way of Examples and Comparative Examples, which, however, never limit the scope of the invention in any way.

EXAMPLE 1

An aqueous alkaline solution having a pH of 11.7 was prepared in a glass flask of 5 liter capacity by dissolving 18 g of n-butylamine in 3717 g of deionized water having an electric conductivity not exceeding 0.1 mS/m. Further, the aqueous solution was admixed with magnesium chloride hexahydrate in an amount of 0.077 g to give a magnesium ion concentration of $1 \times 10^{-4}$ mole/liter in the solution and the aqueous solution was kept at a temperature of 20° C. While controlling the temperature in the range from 5 to 20° C., 765 g of methyl trimethoxysilane were added to the aqueous solution dropwise over a period of 7 hours under agitation with an anchor-blade stirrer rotated at 130 rpm. After completion of the dropwise addition of the silane compound, agitation of the reaction mixture was further continued for additional 60 minutes at a temperature of 60° C. to complete the reaction. The thus obtained aqueous dispersion of particles was subjected to solid-liquid separation by filtration through a pressurizable filter to give wet cakes of the particles containing about 30% of water. The wet cakes were dried in a hot air-circulation oven at 105° C. into a loosely caked dry mass of the particles which was disintegrated by using a jet mill into discrete silicone resin particles. As inspected under an optical microscope, these particles had a good globular particle configuration. Further, the particles were dispersed in methanol and subjected to the measurement of the average particle diameter by using a granulometric instrument (Model Granulometer 850, manufactured by CILAS Alcatel Co.) to find a value of 5.3 μm.

EXAMPLE 2

The experimental procedure for the preparation of silicone resin particles was substantially the same as in Example 1 excepting for the increase of the amount of magnesium chloride hexahydrate from 0.077 g to 0.77 g to give a magnesium ion concentration of $1\times10^{-3}$ mole/liter in the aqueous solution. The thus obtained silicone resin particles had a good globular particle configuration and the average particle diameter thereof was 6.7 µm.

EXAMPLE 3

The experimental procedure for the preparation of silicone resin particles was substantially the same as in Example 1 except that the amount of the deionized water was 3712 g instead of 3717 g and 18 g of n-butylamine were replaced with 23 g of n-propylamine so that the aqueous alkaline solution had a pH of 11.8. The thus obtained silicone resin particles had a good globular particle configuration and the average particle diameter thereof was 4.3 µm.

EXAMPLE 4

The experimental procedure for the preparation of silicone resin particles was substantially the same as in Example 3 excepting for the replacement of the n-propylamine with the same amount of n-pentylamine. The aqueous alkaline solution had a pH of 11.8. The thus obtained silicone resin particles had a good globular particle configuration and the average particle diameter thereof was 6.0 µm.

EXAMPLE 5

The experimental procedure for the preparation of silicone resin particles was about the same as in Example 1 but by employing phenyl trimethoxysilane in place of methyl trimethoxysilane. Thus, an aqueous alkaline solution was prepared by adding 72 g of a 28% ammonia water to 3078 g of the deionized water to give a pH value of 11.8 followed by the addition of 0.063 g of magnesium chloride hexahydrate to give a magnesium ion concentration of $1\times10^{-4}$ mole/liter. The subsequent procedure was substantially the same as in Example 1 excepting for the replacement of 765 g of methyl trimethoxysilane with 1350 g of phenyl trimethoxysilane. The aqueous alkaline solution had a pH of 11.8. The thus obtained silicone resin particles had a good globular particle configuration and the average particle diameter thereof was 5.7 µm.

COMPARATIVE EXAMPLE 1

The experimental procedure for the preparation of silicone resin particles was substantially the same as in Example 1 excepting for the omission of the magnesium chloride in the preparation of the aqueous medium which had a pH of 11.8. Thus obtained silicone resin particles had a good globular particle configuration but the average particle diameter thereof was 1.6 µm.

COMPARATIVE EXAMPLE 2

The experimental procedure for the preparation of silicone resin particles was substantially the same as in Example 5 excepting for the omission of the magnesium chloride in the preparation of the aqueous medium which had a pH of 11.8. Thus obtained silicone resin particles had a good globular particle configuration but the average particle diameter thereof was 1.3 µm.

COMPARATIVE EXAMPLE 3

The experimental procedure was substantially the same as in Example 1 except that the amount of the magnesium chloride hexahydrate was increased from 0.077 g to 15 g to give a magnesium ion concentration of $2\times10^{-2}$ mole/liter in the aqueous alkaline solution. However, the dropwise addition of methyl trimethoxysilane to the aqueous reaction medium could not be continued to the end because appearance of agglomerates was detected in the reaction mixture in the course of dropwise addition of the silane compound and the reaction mixture was converted into a gel-like mass by further continuing addition of the silane compound.

What is claimed is:

1. A method for the preparation of globular particles of a silicone resin which comprises the steps of:
    (a) preparing an aqueous alkaline solution having a pH value in the range from 10.5 to 12.5 by the addition of a basic compound selected from the group consisting of ammonia and water-soluble amine compounds to water;
    (b) adding a water-soluble magnesium salt to the aqueous alkaline solution, in a concentration of the metallic ions in the range from $1\times10^{-5}$ to $1\times10^{-2}$ mole/liter; and
    (c) adding, to the aqueous alkaline solution, an organotrialkoxy silane compound or a partial hydrolysis condensation product thereof as the starting material, in an amount in the range from 5 to 100 parts by weight per 100 parts by weight of the aqueous alkaline solution within a time from 30 minutes to 100 hours, under agitation to effect hydrolysis condensation reaction of the starting material.

2. The method for the preparation of globular particles of a silicone resin as claimed in claim 1 in which the basic compound is an amine compound.

3. The method for the preparation of globular particles of a silicone resin as claimed in claim 2 in which the amine compound is a mono(n-alkyl)amine compound.

4. The method for the preparation of globular particles of a silicone resin as claimed in claim 1 in which the concentration of the metallic ions in the aqueous alkaline solution is in the range from $5\times10^{-5}$ to $5\times10^{-3}$ mole/liter.

5. The method for the preparation of globular particles of a silicone resin as claimed in claim 1 in which the temperature of the aqueous alkaline solution in step (c) is in the range from 0 to 40°C.

6. A method for the preparation of globular particles of a silicone resin which comprises the steps of:
    (a) preparing an aqueous alkaline solution having a pH value in the range from 10.5 to 12.5 by the addition of a basic compound selected from the group consisting of ammonia and water-soluble amine compounds to water;
    (b) adding a water-soluble magnesium salt to the aqueous alkaline solution in a concentration of the metallic ions in the range from $1\times10^{-5}$ to $1\times10^{-2}$ mole/liter; and
    (c) adding, to the aqueous alkaline solution, an organotrialkoxy silane compound or a partial hydrolysis condensation product thereof as the starting material, in an amount in the range from 5 to 100 parts by weight per 100 parts by weight of the aqueous alkaline solution, within a time from 30 minutes to 100 hours, under agitation, at an intensity which does not increase the agglomeration of the globular particles formed, to effect hydrolysis condensation reaction of the starting material.

* * * * *